(12) United States Patent
Randolph (10) Patent No.: US 8,663,132 B2
(45) Date of Patent: Mar. 4, 2014

(54) REDUCED-PRESSURE TREATMENT SYSTEMS AND METHODS EMPLOYING A VARIABLE COVER

(75) Inventor: Larry Tab Randolph, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 416 days.

(21) Appl. No.: 12/758,607

(22) Filed: Apr. 12, 2010

(65) Prior Publication Data

US 2010/0268128 A1  Oct. 21, 2010

Related U.S. Application Data

(60) Provisional application No. 61/169,104, filed on Apr. 14, 2009.

(51) Int. Cl.
 *A61F 13/00* (2006.01)
 *A61M 27/00* (2006.01)

(52) U.S. Cl.
 USPC .............................................. 601/6; 604/543

(58) Field of Classification Search
 USPC ................ 604/543, 540, 304–317, 77; 601/6; 602/41–43, 46, 48, 52–54, 56
 See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," *Current Problems in Modem Clinical Surgery: Interdepartmental Collection*, edited by V. Ye Volkov et al. (Chuvashia State University, Cheboksary, U.S.S.R. 1986);pp. 94-96.

(Continued)

*Primary Examiner* — Jackie Ho
*Assistant Examiner* — Mark Wardas (57) ABSTRACT

A system, dressing, and method for providing reduced pressure treatment to a tissue site on a wound bed of a patient includes a variable wound dressing having a variable cover that is pliable at ambient pressure and less-pliable when placed under reduced pressure. The variable wound dressing has a first side and a second, patient-facing side, and in use, a treatment space is formed between the second, patient-facing side of the variable dressing and the wound bed. One or more ports are used to supply reduced pressure within the variable cover and to the wound site. A reduced-pressure subsystem is also included that is operable to supply reduced pressure to the one or more ports.

23 Claims, 4 Drawing Sheets

(56) References Cited

U.S. PATENT DOCUMENTS

| | | | |
|---|---|---|---|
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,745,998 A | 7/1973 | Rose | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,701,917 A | 12/1997 | Khouri | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,491,693 B1 | 12/2002 | Lytinas | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,169,151 B1 | 1/2007 | Lytinas | |
| 7,381,859 B2* | 6/2008 | Hunt et al. | 602/46 |
| 7,775,213 B2* | 8/2010 | Henke-Sarmento et al. | 128/852 |
| 8,142,419 B2* | 3/2012 | Heaton et al. | 604/540 |
| 8,188,331 B2* | 5/2012 | Barta et al. | 602/53 |
| 2001/0043943 A1 | 11/2001 | Coffey | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2004/0073152 A1* | 4/2004 | Karason et al. | 602/41 |
| 2005/0137513 A1* | 6/2005 | Rugfelt | 602/41 |
| 2005/0137539 A1 | 6/2005 | Biggie | |
| 2010/0106106 A1* | 4/2010 | Heaton et al. | 604/290 |
| 2013/0096518 A1* | 4/2013 | Hall et al. | 604/319 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| EP | 1994954 A1 | 11/2008 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 01/89431 A1 | 11/2001 |
| WO | WO 2009/114624 A2 | 9/2009 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

(56) References Cited

OTHER PUBLICATIONS

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Ðivadinović, V. Žukić, Ð. Maksimović, Ð. Radak, and P. Peška, "Vacuum Therapy in the Treatment of Peripheral Blood Vessels," *Timok Medical Journal* 11 (1986), pp. 161-164.

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

International Search Report and Written Opinion date mailed Jul. 30, 2010; PCT Application No. PCT/US2010/030888.

* cited by examiner

REDUCED-PRESSURE TREATMENT SYSTEMS AND METHODS EMPLOYING A VARIABLE COVER

RELATED APPLICATION

The present invention claims the benefit, under 35 USC §119(e), of the filing of U.S. Provisional Patent Application Ser. No. 61/169,104, entitled "Reduced-Pressure Treatment Systems and Methods Employing A Variable Cover," filed Apr. 14, 2009, which is incorporated herein by reference for all purposes.

BACKGROUND

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Unless otherwise indicated, as used herein, "or" does not require mutual exclusivity.

SUMMARY

The reduced-pressure treatment systems and methods herein address shortcomings of prior treatment systems and methods. According to an illustrative embodiment, a system for providing reduced-pressure treatment to a tissue site on a wound bed of a patient includes a variable wound dressing having a variable cover that is pliable at ambient pressure and less pliable when placed under reduced pressure. The variable wound dressing has a first side and a second, patient-facing side, and a treatment space is formed between the second, patient-facing side of the variable dressing and the wound bed. A first reduced-pressure port is in fluid communication with the variable cover and operable to supply reduced pressure within the variable cover. Also, a second reduced-pressure port is in fluid communication with the treatment space. A reduced-pressure subsystem is also included that is operable to supply reduced pressure to the first reduced-pressure port and the second reduced-pressure port.

According to another illustrative embodiment, a method for providing reduced pressure treatment to a tissue site on a wound bed of a patient is provided. The method includes the step of providing a variable wound dressing having an interior space. The variable wound dressing has a pliable state and a less-pliable state and is operable to change from the pliable state to the less-pliable state in the presence of an activating reduced pressure. The method also includes the step of disposing the variable wound dressing over the wound, whereby a treatment space is formed between the wound and the variable wound dressing. The method also includes the steps of forming a fluid seal over the wound, providing an activating reduced pressure to the interior space of the variable wound dressing, and providing a treatment reduced pressure to the treatment space.

According to another illustrative embodiment, a method of manufacturing a variable wound dressing for use as part of a reduced-pressure wound treatment system is provided. The method includes the step of providing an envelope having an interior space and having a first side and a second, patient-facing side. The method also includes disposing a plurality of spacing members within the interior space, and sealing the interior space. In addition, the method may include forming a first reduced-pressure aperture on the envelope for providing fluid communication to the interior space and forming a second reduced-pressure aperture through the envelope for providing fluid communication from the first side of the envelope to the second side of the envelope.

Other objects, features, and advantages of the illustrative embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
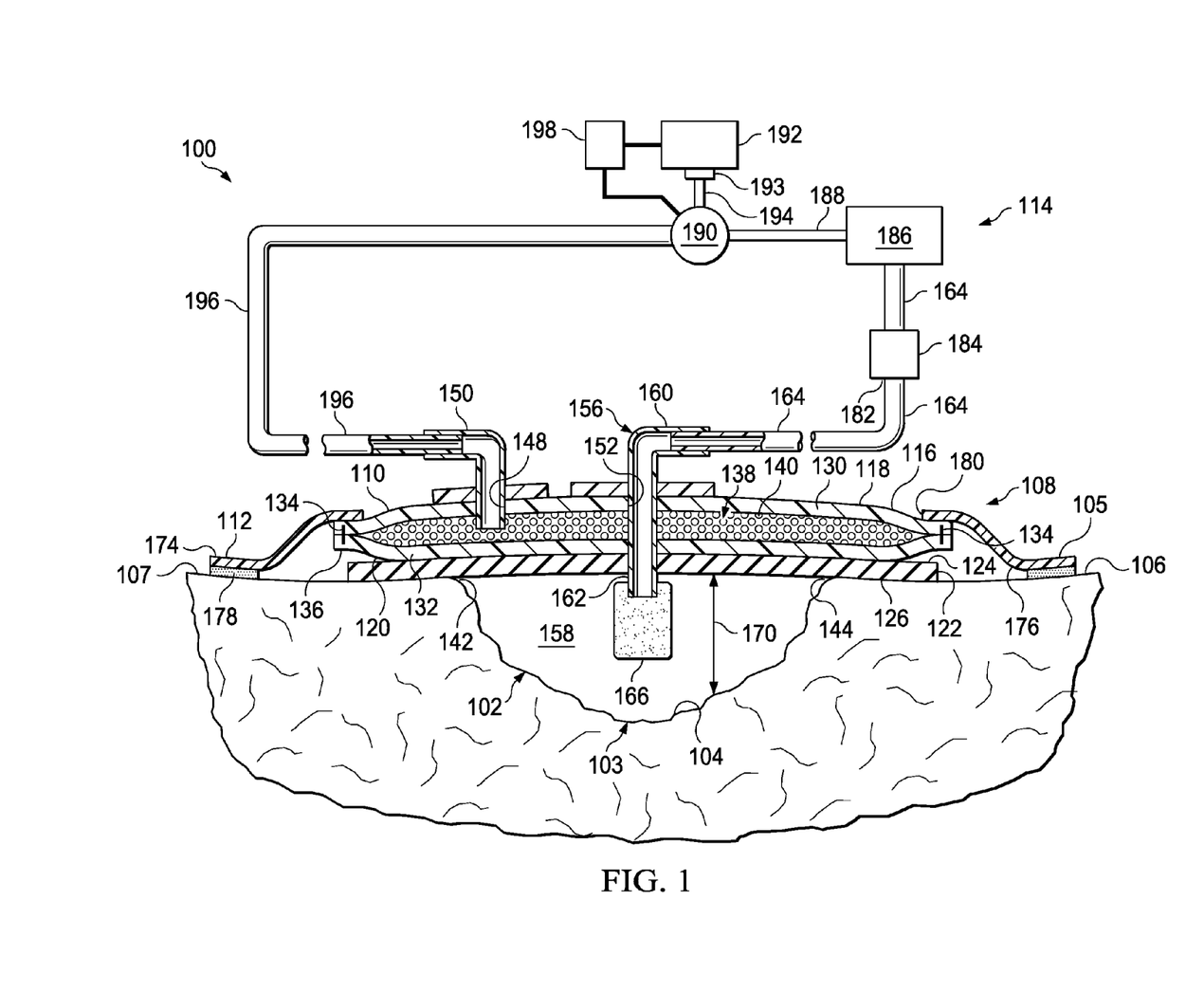
FIG. 1 is a schematic, cross-sectional view, with a portion shown as a block diagram, of a reduced-pressure treatment system according to one illustrative embodiment.

Referring to FIG. 1, an illustrative embodiment of a reduced-pressure treatment system 100 for providing reduced-pressure treatment to a tissue site 103, which may include a wound 102, in a wound bed 104 of a patient 106 is presented. The reduced-pressure treatment system 100 includes a variable wound dressing 108, which includes a variable cover 110, an over-drape 112, and a reduced-pressure subsystem 114.

As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. In one embodiment, the reduced pressure may initially generate fluid flow in a first reduced-pressure delivery conduit 164. Unless otherwise indicated, values of pressure stated herein are gauge pressures. The reduced pressure delivered may be constant or variable (patterned or random) and may be delivered continuously or intermittently. Although the terms "vacuum" and "negative pressure" may be used to describe the pressure applied to the tissue site 103, the actual pressure applied to the tissue site 103 may be more than the pressure normally associated with a complete vacuum. Consistent with the use herein, an increase in reduced pressure or vacuum pressure typically refers to a relative reduction in absolute pressure.

The wound 102 may be any type of wound, or damaged area of tissue, and may include wounds from trauma, surgery, or other causes, such as a diabetic ulcer. The tissue site 103, which includes the wound 102, may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 103 may include removal of fluids, e.g., ascites or exudates, protection of the abdominal cavity, or delivery of reduced pressure.

The variable wound dressing 108, or treatment device, includes the variable cover 110. The variable cover 110 is formed with a sealed envelope 116 that has a first side 118 and a second, patient-facing side 120. The variable wound dressing 108 may further include a support member 122, which has a first side 124 and a second, patient-facing side 126. The support member 122 may be a separate item or may be coupled to the second, patient-facing side 120 of the variable cover 110 or formed integrally with the second, patient-facing side 120 of the variable cover 110. As will be explained further below, the support member 122 provides initial support for the variable cover 110.

The sealed envelope 116 is formed by a first wall 130, which may be a first sheet, and a second wall 132, which may be a second sheet. The first wall 130 and second wall 132 may be coupled, such as by a weld 134, on a peripheral edge 136. The coupling of walls 130 and 132 may be accomplished using any known technique, including welding (e.g., ultra sonic or RF welding), bonding, adhesives, cements, etc. An interior space 138 within the sealed envelope 116 is formed between the first wall 130 and the second wall 132. A plurality of spacing members 140 is disposed within the interior space 138. The first wall 130 and the second wall 132 may be formed of a non-breathable material, such as a non-breathable nylon material or a resilient polymer film. The material from which the first wall 130 and second wall 132 are formed may further have the characteristic of being substantially non-stretchable. In an alternative embodiment (not shown), partitioning members may be placed within the interior space 138 to hold a portion of the spacing members 140 in a designated zone within the interior space 138.

The spacing members 140 are formed from a material such that when the spacing members 140 are subjected to reduced pressure within the variable cover 110, the variable cover 110 becomes less pliable, or more rigid. The increase in rigidity, or decrease in pliability, may occur because contact forces between adjacent spacing members 140 increases under reduced pressure and thereby causes an increase in frictional forces that oppose relative movement of the spacing members 140. The friction between the spacing members 140 makes the variable cover 110 become less pliable, or more rigid. Alternatively, the increased forces between spacing members 140 may cause a mechanical lock in some embodiments.

The spacing members 140 may include, for example, polystyrene members, including polystyrene balls, that may be encased in a laminated nylon and vinyl material, styrofoam beads, low-density polymer beads, solid granules of plastic, etc. The spacing members 140 may take any shape, but round members may allow easier relative movement while the variable wound dressing 108 is being shaped or while the variable wound dressing 108 is in a pliable state.

When reduced pressure is applied to the interior space 138 of the variable cover 110, the variable cover 110 becomes less pliable (more rigid), as the spacing members 140 press against one another. In the less-pliable state (or more rigid state), the variable cover 110 preferably will not substantially deform as treatment reduced pressure is supplied to a treatment space 158. The interior space 138 of the variable cover 110 has a first volume ($V_1$) at a first reduced pressure ($P_1$) and a second volume ($V_2$) at a second reduced pressure ($P_2$), where $P_1$ and $P_2$ are less than atmospheric or ambient pressure and $P_1 > P_2$ on an absolute pressure scale and $V_1 > V_2$. Assuming that $P_2$ is low enough to cause the spacing members 140 to impinge against one another, the variable cover 110 becomes less pliable at the second reduced pressure ($P_2$) than at the first reduced pressure ($P_1$).

The support member 122 may be formed from a thin (e.g., 0.25 mm to 2 mm), high-density polyethylene sheet, but numerous other materials might be used, such as a closed-cell foam. The support member 122 provides support between wound margins 142 and 144 of the variable cover 110, including while the variable cover 110 is being put into place in the pliable state. The support member 122 may prevent the variable cover 110 from sagging excessively while the variable cover 110 is in the pliable state. For example, in one embodiment, the support member 122 may prevent the variable cover 110 from extending below the plane containing wound margins 142 and 144. Thus, the support member 122 preferably has enough structural support to hold the variable cover 110 without deforming below the plane that contains wound margins 142 and 144. The support member 122 is preferably formed from a non-adherent material to provide for the situation in which tissue may be pressed against the support member 122. The support member 122 may have substances applied to the second, patient-facing side 126, such as honey, silver, various anti-microbials, etc.

The substances placed on the second, patient-facing side 126 of support member 122 may help to fight infection, provide other health benefits, or facilitate movement of tissue as the tissue grows while disposed against the second, patient-facing side 126 of the support member 122. A sealing material, e.g., a hydrocolloid, may be added to the second, patient-facing side 126 of the support member 122 to facilitate formation of a fluid seal with the patient's epidermis 107. If a closed-cell foam is used as the support member 122, the closed-cell foam may be impregnated with the substances and may provide for a timed release of the substances. In an alternative embodiment (not explicitly shown) in which the support member 122 is omitted, the substances or substances may be added to second, patient-facing side of the second wall 132.

Reduced pressure is provided to the interior space 138 of the variable cover 110 and to the wound 102. As to the former, a first reduced-pressure aperture 148 is formed on the first side 118 of the variable cover 110, and a first reduced-pressure port 150 is sized and configured to cooperate with the first reduced-pressure aperture 148 to provide reduced pressure to the interior space 138. A second reduced-pressure aperture 152 may be formed through the sealed envelope 116 and particularly through the first wall 130 and the second wall 132. The second reduced-pressure aperture 152 allows a second reduced-pressure port 156 to fluidly communicate with the treatment space 158 that is between the wound bed 104 and the variable wound dressing 108. The second reduced-pressure port 156 may have a first portion 160 and a second portion 162. The first portion 160 fluidly couples the first reduced-pressure delivery conduit 164 to the second reduced-pressure port 156. The second portion 162 may have a wicking member 166 associated with the second portion 162.

The wicking member 166 may be coupled to the second portion 162, such as by bonding or may be held relative to the second portion 162 or by other techniques, such as by an interference fit or fasteners. The wicking member 166 may be any material that facilitates a migration of exudate or other liquids from the tissue site 103 or wound bed 104 to the second reduced-pressure port 156. As one illustrative example, the wicking member 166 may be a reticulated foam member, such as a GranuFoam® material manufactured by Kinetic Concepts, Incorporated of San Antonio, Tex. The wicking member 166 may extend the full vertical (for the orientation shown in FIG. 1) distance 170 between the variable wound dressing 108 and the wound bed 104, or a portion thereof as shown. The wicking member 166 may also extend laterally in varying degrees.

The over-drape 112 may be used over the wound 102 to help form a fluid seal. The over-drape 112 includes a first side 174 and a second, patient-facing side 176. The second, patient-facing side 176 may include an attachment device 178 for attaching the over-drape 112 to a portion of intact epidermis of the patient 106. The attachment device 178 may be used to hold the over-drape 112 against the patient's 106 epidermis or another layer, such as a gasket or additional sealing member. The attachment device 178 may take numerous forms. For example, the attachment device 178 may be a medically acceptable, pressure-sensitive adhesive that extends about a periphery 105 of the over-drape 112. The over-drape 112 may have a central opening 180 or may be a solid sheet with only apertures corresponding to the first reduced-pressure aperture 148 and the second reduced-pressure aperture 152.

The over-drape 112 may be any material that provides a fluid seal. The over-drape 112 may, for example, be an impermeable or semi-permeable, elastomeric material that has pore sizes less than about 20 microns. "Elastomeric" means having the properties of an elastomer. It generally refers to a polymeric material that has rubber-like properties. More specifically, most elastomers have ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Other specific examples of sealing member materials include a silicone drape, 3M Tegaderm® drape, acrylic drape, such as one available from Avery Dennison, or an incise drape.

The reduced-pressure subsystem 114 provides an activation reduced pressure to the first reduced-pressure port 150 and a treatment reduced pressure to the second reduced-pressure port 156. The first reduced-pressure delivery conduit 164 is fluidly coupled to the second reduced-pressure port 156 and delivers treatment reduced pressure thereto. A medial portion 182 of the first reduced-pressure delivery conduit 164 may include a representative device 184, which may be one or more devices to accomplish different tasks. For example, the device 184 may be a supplemental fluid reservoir or collection member to hold exudates and other fluids removed. Other examples of device 184 that may be included on the medial portion 182 of the first reduced-pressure delivery conduit 164 or otherwise fluidly coupled to the first reduced-pressure delivery conduit 164 include the following non-limiting examples: a pressure-feedback device, a volume detection system, a blood detection system, an infection detection system, a flow monitoring system, a temperature monitoring system, etc. Some of these devices may be formed integrally to a reduced-pressure source 192. For example, a reduced-pressure port 193 on the reduced-pressure source 192 may include a filter member that includes one or more filters, e.g., an odor filter.

A canister 186, or reservoir, is fluidly coupled to the first reduced-pressure delivery conduit 164 for receiving exudates and other fluids from the wound 102. A second reduced-pressure delivery conduit 188 is fluidly coupled to a valve 190, such as a three-way valve. The reduced-pressure source 192 generates a reduced pressure that is supplied through a third reduced-pressure delivery conduit 194 to the three-way valve 190. The reduced-pressure source 192 provides reduced pressure. The reduced-pressure source 192 may be any means of supplying a reduced pressure, such as a vacuum pump or wall suction source. While the amount and nature of reduced pressure applied to the tissue site 103 or treatment space 158 will typically vary according to the application, the reduced pressure will typically be between −5 mm Hg and −500 mm Hg, and more typically between −100 mm Hg and −250 mm Hg, and more typically still between −100 mm Hg and −200 mm Hg.

A fourth reduced-pressure delivery conduit 196 is fluidly coupled to the valve 190 and to the first reduced-pressure delivery conduit 164. The valve 190 provides reduced pressure from the reduced-pressure source 192 through the fourth reduced-pressure delivery conduit 196 to the first reduced-pressure port 150 or to the second reduced-pressure delivery conduit 188 and on through the first reduced-pressure delivery conduit 164 to the second reduced-pressure port 156. In an alternative embodiment (not shown), a reduced-pressure source may be associated with the first reduced-pressure port 150 and another reduced-pressure source associated with the second reduced-pressure port 156 without necessitating the need for a valve, such as valve 190. In still another illustrative embodiment, a controller 198 may be provided and coupled to the reduced-pressure source 192 and the valve 190 for controlling the same.

The activation reduced pressure is supplied by the reduced-pressure subsystem 114 through the fourth reduced-pressure delivery conduit 196 to the first reduced-pressure port 150. The activation reduced pressure is at a level adequate to cause the plurality of spacing members 140 within the interior space 138 to be urged against one another and to thereby cause, in turn, the variable cover 110 to become less pliable. The reduced pressure adequate to establish this effect is the activation reduced pressure and is in the range between −50 mm Hg and −500 mm Hg and more preferably −100 and −300 mm Hg and more preferably still −100 and −200 mm Hg.

In operation, the reduced-pressure treatment system 100 is initially applied, depending on the embodiment, by placing the support member 122 over the wound 102 and on a portion of the epidermis 107 to create the treatment space 158. The treatment space 158 is the space between the wound bed 104 and the second, patient-facing side 126 of the support member 122. Then, if not integrally formed with the support member 122, the variable cover 110 is deployed adjacent to the support member 122. Typically, the over-drape 112 is then deployed.

The over-drape 112 cooperates with or is applied over at least a portion of the variable cover 110 to provide a fluid seal over the tissue site 103. It should be noted that during the application of the variable cover 110, the variable cover 110 is typically in the pliable state and may be readily moved into a desired location by the healthcare provider without the variable cover 110 interfering with the wound 102. If not already installed, the first reduced-pressure port 150 may then be placed into the first reduced-pressure aperture 148. The first reduced-pressure port 150 is coupled to the fourth reduced-pressure delivery conduit 196. If not already installed, the second reduced-pressure port 156 is placed through the second reduced-pressure aperture 152. The s coupled second reduced-pressure port 156 is coupled to the first reduced-pressure delivery conduit 164. If not already associated, the wicking member 166 may be associated with the second portion 162 of the second reduced-pressure port 156. The reduced-pressure subsystem 114 may then be activated to provide reduced-pressure to the reduced-pressure subsystem 114.

On initial activation, the reduced-pressure source 192 begins to supply reduced pressure which is delivered through the valve 190 to the fourth reduced-pressure delivery conduit 196 and into the interior space 138 such that the reduced pressure, which is the activation reduced pressure, causes the variable cover 110 to become less pliable, i.e., variable cover 110 enters the less-pliable state (or more rigid state). Once the variable cover 110 is in the rigid state, or less-pliable state, the valve 190 is selected to deliver reduced pressure through the second reduced-pressure delivery conduit 188 and on through the first reduced-pressure delivery conduit 164 to the second reduced-pressure port 156 and into the treatment space 158. Alternatively, the valve 190 may provide reduced pressure to the second reduced-pressure delivery conduit 188 at the same time.

The treatment reduced pressure supplied to the treatment space 158 provides treatment to the tissue site 103 and wound 102 and helps to remove exudates and other fluids. In some instances, the wound 102 may be placed under the influence of reduced pressure proximate to the second portion 162 of the second reduced-pressure port 156 and in any event will be placed proximate to the wicking member 166. The wicking member 166 helps deliver reduced pressure to the wound and helps to deliver exudate or other fluids into the second reduced-pressure port 156.

Because the treatment space 158 does not require a manifolding member or other structure when the variable wound dressing 108 is used, the need to change the variable wound dressing 108 may be reduced or eliminated. Moreover, because in the less-pliable state, the variable wound dressing 108 does not develop an inward force on the wound margins 142, 144, growth of tissue at the wound margins 142, 144 may occur without inhibition. The ability of the variable cover 110 to transition between flexible and rigid or semi-rigid states facilitates application and use of the variable wound dressing 108.

Figure 2A:
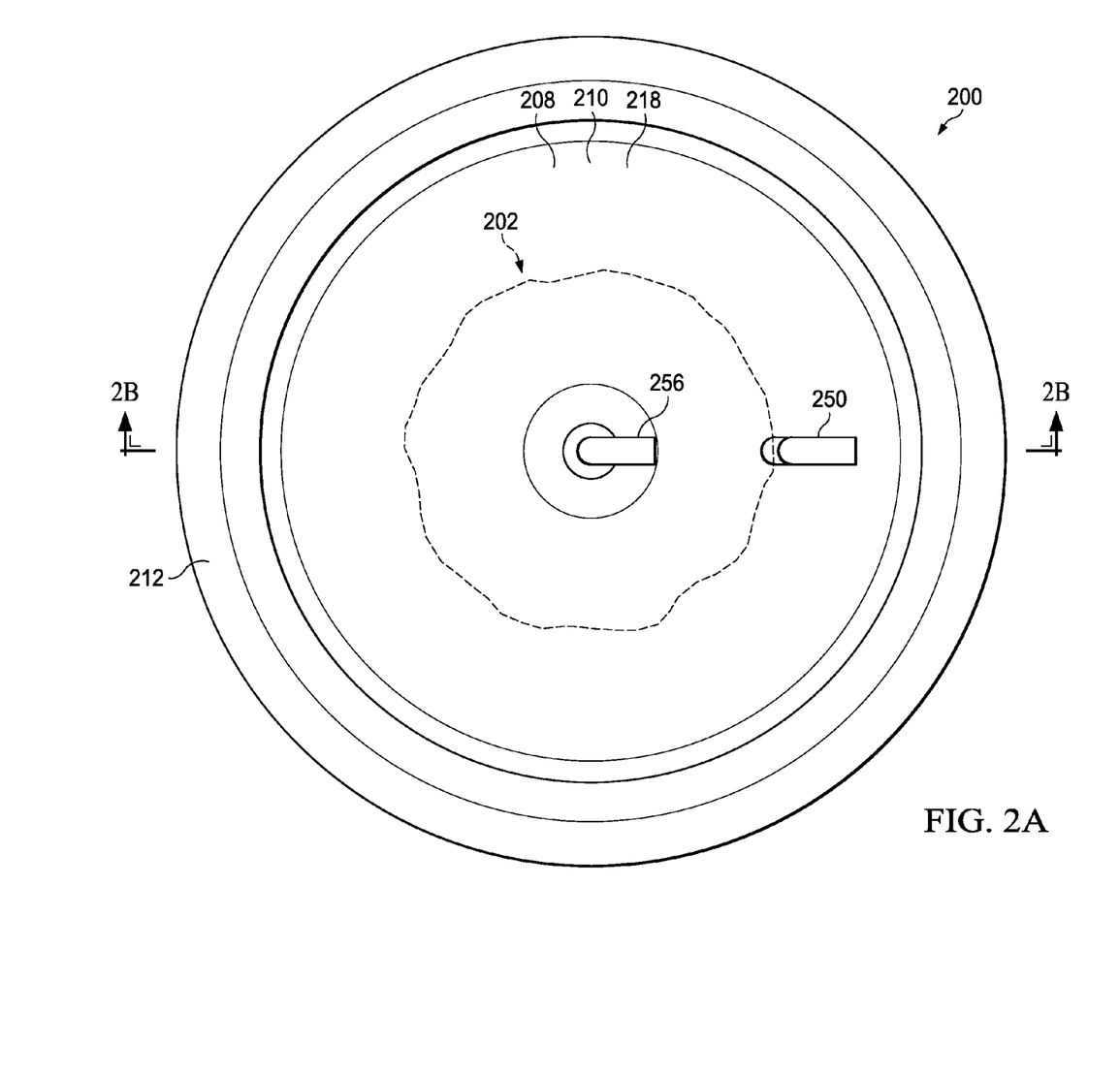
FIG. 2A is a schematic, plan view of an illustrative embodiment of a reduced-pressure treatment system.
Figure 2B:
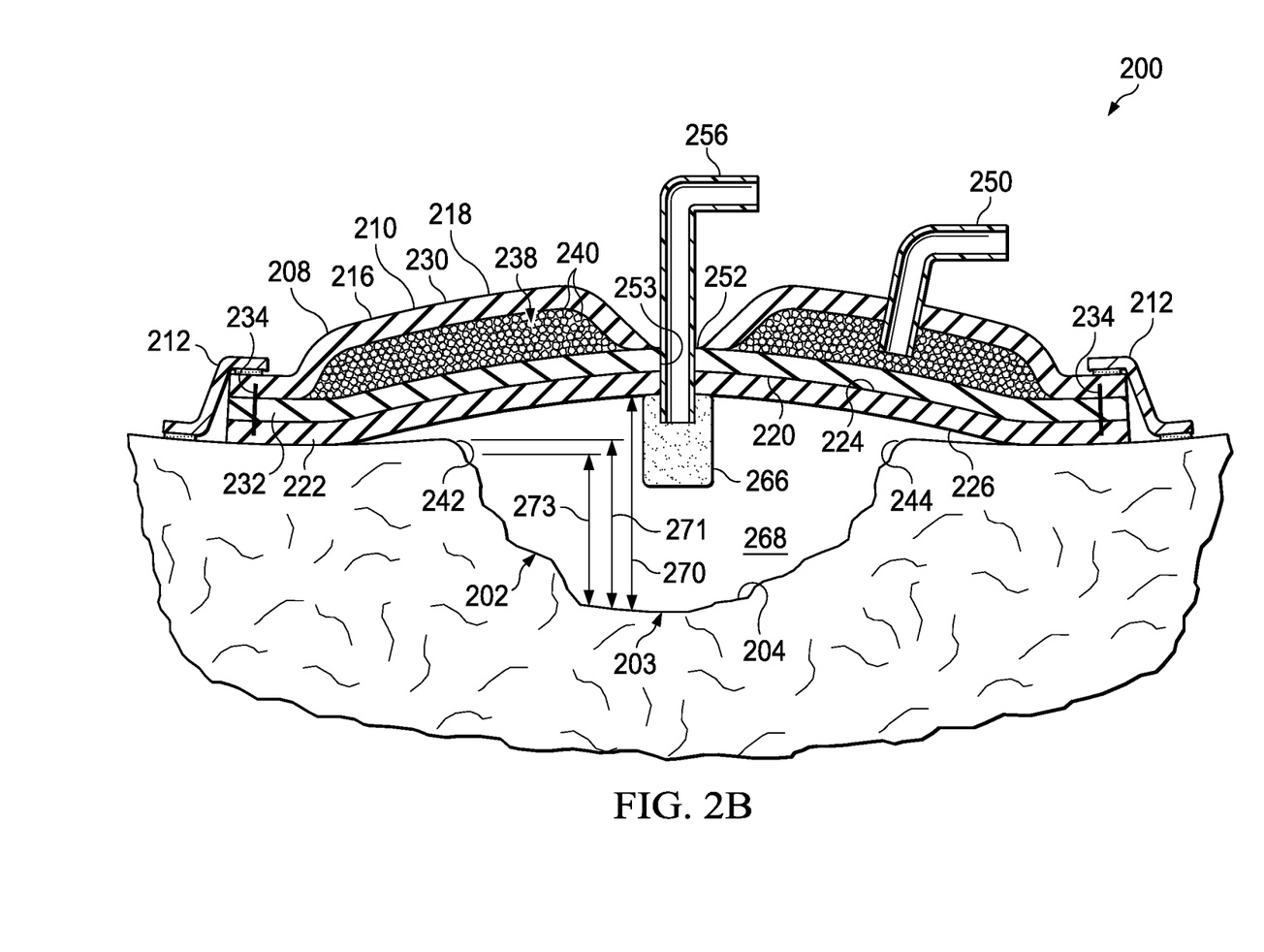
FIG. 2B is a schematic, cross-sectional view taken along line 2B-2B in FIG. 2A.

Referring now to FIGS. 2A and 2B, another illustrative embodiment of a reduced-pressure treatment system 200 is presented. The reduced-pressure treatment system 200 is analogous in most respects to the reduced-pressure treatment system 100 of FIG. 1 and analogous parts have been shown by indexing the reference numerals by 100. Thus, for example, the reduced-pressure treatment system 200 is shown over a tissue site 203, which includes a wound 202, and sealed with an over-drape 212. A first reduced-pressure port 250 is shown extending from a first side 218 of a variable cover 210. A second reduced-pressure port 256 is shown with a wicking member 266. At the same time, there are a number of differences.

For example, in this illustrative embodiment, the variable cover 210 is formed with an interior space 238 into which a plurality of spacing members 240 is disposed, but in this illustrative embodiment, the spacing members 240 are formed as irregular-shaped members. In this regard, it should be noted that the spacing members 140, 240 may take any shape. In this illustrative embodiment, a support member 222 is coupled to the variable cover 210. The support member 222 may be coupled on a first side 224 to a second, patient-facing side 220 of a sealed envelope 216 of the variable cover 210. Alternatively, as shown, a periphery, e.g., near where weld 234 is located, of the sealed envelope 216 and support member 222 may be coupled. The coupling for either approach may occur using any known technique, such as bonding, welding, adhesives, etc. In FIG. 2B, the coupling is shown with the weld 234 coupling the support member 222 and a second wall 232 of the sealed envelope 216. The weld 234 in this embodiment also couples a first wall 230 and the second wall 232 to form the sealed envelope 216.

FIG. 2B shows that the variable wound dressing 208 may be manipulated into having a dome shape, which may give additional structural support in order to provide and maintain the treatment space 268 under increased reduced pressure. Thus, for example, the distance between the wound bed 204 and the second, patient-facing side 226 of the support member 222 is given by the distance 270, which is greater than the distance would be with a substantially flat configuration, which would correspond with distance 271. For comparison purposes, it should also be noted that without the support member 222, the weight of the variable wound dressing 208 might cause the variable wound dressing 208 to extend below the plane of the wound margins 242 and 244 as suggested by distance 273.

In the illustrative embodiment of FIG. 2B, the second reduced-pressure aperture 252 is formed on a web portion 253 of the variable cover 210. The web portion 253 is formed by bringing the first wall 230 into contact or close proximity to the second wall 232 in a given area so as to minimize or eliminate the interior space 238 proximate the second reduced-pressure aperture 252.

Figure 3:
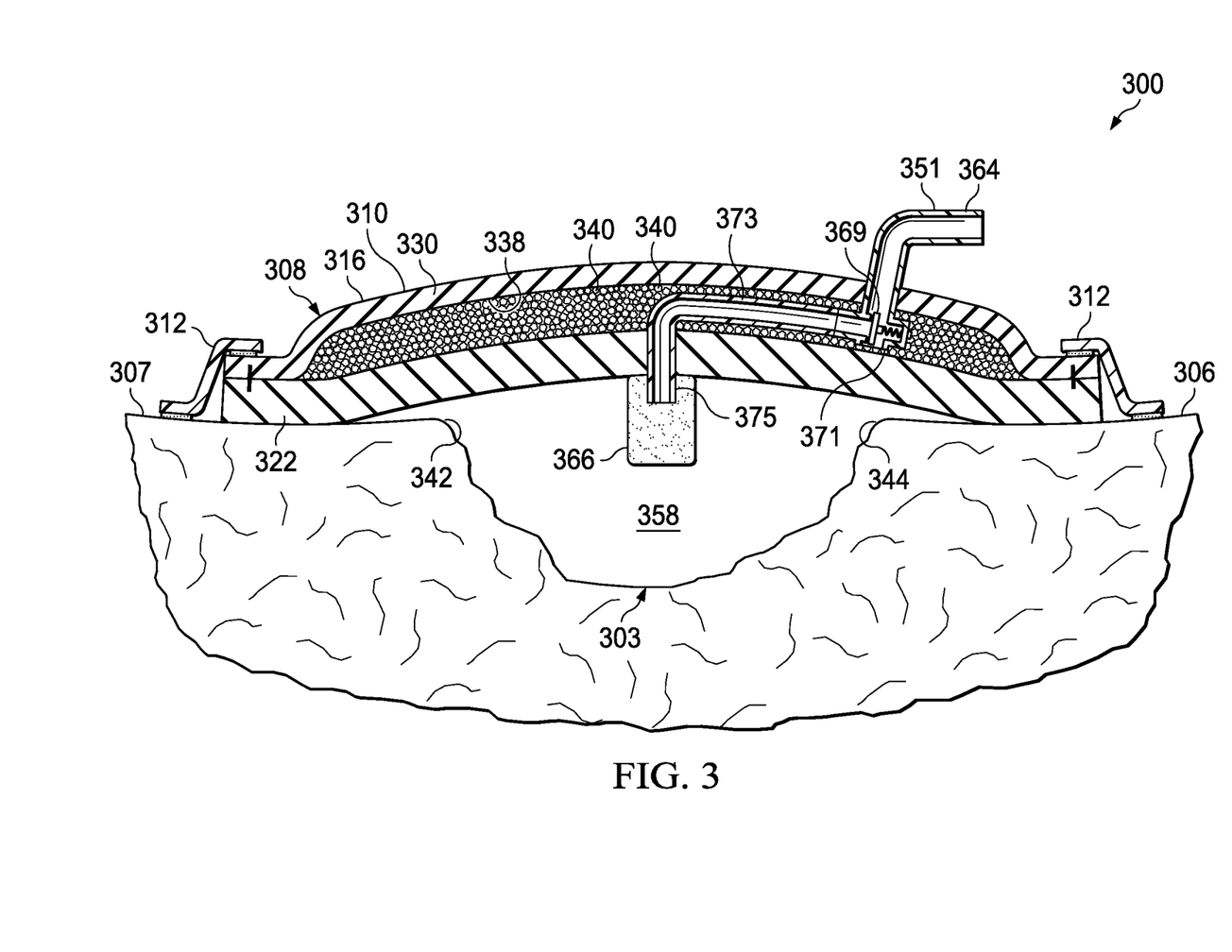
FIG. 3 is a schematic, cross-sectional view of a portion of a reduced-pressure treatment system according to another illustrative embodiment.

Referring now to FIG. 3, an alternative embodiment of a portion of a reduced-pressure treatment system 300 is presented. The reduced-pressure treatment system 300 is analogous in most respects to the reduced-pressure treatment system 100 of FIG. 1, and to indicate generally analogous parts, reference numerals have been indexed by 200. Thus, a variable wound dressing 308 is shown on a portion of epidermis 307 of a patient 306. The variable wound dressing 308 has a variable wound cover 310 that extends across wound margins 342, 344 and covers a tissue site 303. The variable wound cover 310 is positioned over the tissue site 303 and thereby helps define a treatment space 358. An overdrape 312 provides a fluid seal between the variable wound cover 310 and the patient's epidermis 307.

The variable wound cover 310 is formed with a sealed envelope 316 that defines an interior space 338 containing a plurality of spacing members 340. The sealed envelope 316 may be formed by a first wall 330 and a second wall 322. It should be noted that in this particular embodiment, the second wall 322 serves as both a sealing wall and a support member. In other words, by comparison with FIG. 1, the second wall 132 has a support member 122 placed adjacent to the second wall 132, but in the embodiment of FIG. 3, the wall and support member are integrally formed.

The reduced-pressure treatment system 300 also differs in that the reduced-pressure treatment system 300 has a single reduced-pressure delivery conduit 364 that provides reduced pressure to a reduced-pressure port 351, or interface. The reduced-pressure port 351 directly or in combination with additional conduit members provides reduced pressure to a pressure management device, such as a pop valve 369. The pop valve 369 allows reduced pressure below a reduced-pressure threshold (RPT) to be delivered to the interior space 338 through a conduit exit 371. Any number of pop valve arrangements may be used for the pop valve 369.

Functionally, the pop valve 369 allows reduced pressure to evacuate the interior space 338 sufficiently to cause the variable wound cover 310 to enter the rigid state (less-pliable state) before a deforming load is placed on the variable wound cover 310 by reduced pressure being delivered to the treatment space 358. When the reduced pressure delivered by the reduced-pressure port 351 exceeds the reduced-pressure threshold (RPT), e.g., increases beyond −100 mm Hg, a −150 mm Hg, or other RPT, a portion of the pop valve 369 allows reduced pressure to enter a reduced-pressure conduit 373 and thereby is delivered to the treatment space 358 through a second reduced-pressure exit 375. A wicking member 366 may be associated with the second reduced-pressure exit 375. With the arrangement shown for the reduced-pressure treatment system 300, a single reduced-pressure source may be utilized and the variable wound cover 310 will enter the rigid state (less-pliable state) before a reduced pressure is delivered to the treatment space 358.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

What is claimed is:

1. A method for providing reduced-pressure treatment to a wound bed at a tissue site, the method comprising the steps of: providing a sealed envelope having a first side, a second side, and an interior space, the interior space having a plurality of polymer granules, beads, or balls disposed therein; disposing the sealed envelope over the tissue site to form a treatment space between the wound bed and the sealed envelope; forming a fluid seal over the tissue site; providing reduced pressure to the interior space of the sealed envelope to decrease a volume of the interior space and make the sealed envelope more rigid; and providing reduced pressure to the treatment space.

2. The method of claim 1, further comprising the step of disposing a wicking member in the treatment space.

3. The method of claim 1, further comprising the step of disposing a support member over the tissue site.

4. The method of claim 1, wherein the step of disposing the sealed envelope over the tissue site comprises the steps of disposing a support member over the tissue site and disposing the sealed envelope over the support member.

5. The method of claim 1, wherein the step of forming a fluid seal over the tissue site comprises applying an over-drape over at least a portion of the sealed envelope to form a fluid seal between the sealed envelope and the tissue site.

6. The method of claim 1, wherein the interior space is fluidly sealed from the tissue site.

7. A variable wound dressing for treating a wound bed at a tissue site comprising: a sealed envelope having a first wall coupled to a second wall to define an interior space between a portion of the first wall and a portion of the second wall; a plurality of polymer granules, beads, or balls disposed within the interior space of the sealed envelope; and a reduced-pressure port in fluid communication with the interior space and operable to provide reduced pressure to the interior space from a source of reduced pressure to decrease a volume of the interior space and cause the sealed envelope to become more rigid, wherein the reduced pressure port comprises a first reduced pressure port and a second reduced pressure port, and wherein the second reduced pressure port extends through the sealed envelope.

8. The variable, reduced-pressure wound dressing of claim 7, further comprising:
a reduced-pressure port in fluid communication with the interior space and in fluid communication with the tissue-facing side of the variable cover.

9. The variable wound dressing of claim 7, wherein the interior space has a first volume ($V_1$) at a first reduced pressure ($P_1$) and a second volume ($V_2$) at a second reduced pressure ($P_2$), and wherein $P_1 > P_2$ on an absolute pressure scale and $V_1 > V_2$.

10. The variable wound dressing of claim 9 wherein the sealed envelope is more rigid at the second reduced pressure ($P_2$) than the first reduced pressure ($P_1$).

11. The variable wound dressing of claim 7, further comprising a support member having a first side and a second side, and wherein the first side of the support member is coupled to the second wall of the sealed envelope to support the sealed envelope when positioned at the tissue site without reduced pressure being supplied.

12. The variable wound dressing of claim 11, wherein the support member comprises a high-density polyethylene sheet.

13. The variable wound dressing of claim 7, wherein the interior space is fluidly sealed from the tissue site.

14. A system for providing reduced-pressure treatment to a wound bed at a tissue site comprising: a variable wound dressing-comprising a sealed envelope having a first side, a second side, and an interior space, the second side forming a treatment space with the wound bed when the sealed envelope is positioned at the tissue site, the variable wound dressing further comprising a plurality of polymer granules, beads, or balls disposed within the interior space and adapted to cause the sealed envelope to become more rigid when a reduced pressure is applied to the interior space; a first reduced-pressure port in fluid communication with the interior space, and operable to provide reduced pressure to the interior space from a source of reduced pressure to decrease a volume of the interior space; a second reduced-pressure port extending through the sealed envelope and adapted to be in fluid communication with the treatment space when the sealed member is positioned at the tissue site, and operable to provide reduced pressure to the treatment space from a source a reduced pressure; and a reduced-pressure subsystem operable to supply reduced pressure to the first reduced-pressure port and the second reduced-pressure port.

15. The system of claim 14, wherein the second reduced-pressure port has a first portion and a second portion, and further comprising a wicking member associated with the second portion of the second reduced-pressure port.

16. The system of claim 14, wherein the variable wound dressing further comprises a support member adjacent the second side of the sealed envelope to support the sealed envelope when positioned at the tissue site without reduced pressure being supplied.

17. The system of claim 16, wherein the support member is coupled to the second-side of the sealed envelope.

18. The system of claim 14, wherein the solid members comprise a plurality of polymer beads.

19. The system of claim 14, wherein the solid members comprise a plurality of polystyrene balls.

20. The system of claim 14, wherein the reduced-pressure subsystem comprises:
- a reduced-pressure source;
- a three-way valve fluidly coupled to the reduced-pressure source, the first reduced-pressure port, and the second reduced-pressure port; and
- wherein the three-way valve is operable to provide reduced-pressure to the first reduced-pressure port and the second reduced-pressure port.

21. The system of claim 14, further comprising an overdrape for sealing at least a portion of the sealed envelope to the tissue site.

22. The system of claim 14, wherein:
- the second reduced-pressure port has a first portion and a second portion, and further comprising a wicking member associated with the second portion of the second reduced-pressure port; and
- the variable wound dressing further comprises a support member adjacent the second side of the sealed envelope to support the sealed envelope when positioned at the tissue site without reduced pressure being supplied.

23. The system of claim 14, wherein the first reduced-pressure port and the second reduced-pressure port comprises a single reduced-pressure port having a valve.

\* \* \* \* \*